United States Patent [19]

Manghisi et al.

[11] 4,115,585

[45] Sep. 19, 1978

[54] ESTERS OF 1-(P-HYDROXYPHENYL)-2-(1'-METHYL-2'-PHENOXYETHYLAMINO)-1-PROPANOL

[75] Inventors: Elso Manghisi, Monza (Milan); Aldo Salimbeni, Milan; Giovanni Ferni, Cusano Milanino (Milan), all of Italy

[73] Assignee: Instituto Luso Farmaco d'Italia S.r.l., Milan, Italy

[21] Appl. No.: 795,543

[22] Filed: May 10, 1977

[30] Foreign Application Priority Data

May 17, 1976 [IT]  Italy .................................. 23347/76
Mar. 28, 1977 [IT]  Italy .................................. 21735/77

[51] Int. Cl.² .................. A61K 31/24; C07C 93/26
[52] U.S. Cl. .................................... 424/311; 560/138
[58] Field of Search ................ 260/479 R; 424/311; 560/138

[56] References Cited

U.S. PATENT DOCUMENTS

| 3,461,164 | 8/1969 | Schulte et al. | 260/479 R |
| 3,657,244 | 4/1972 | Menthrup et al. | 260/479 |
| 3,825,583 | 7/1974 | Hussain et al. | 260/479 R |

FOREIGN PATENT DOCUMENTS

2,357,748  6/1974  Fed. Rep. of Germany ........... 260/479

OTHER PUBLICATIONS

The Merck Index, Eighth Edition, p. 594 (1968).

*Primary Examiner*—Jane S. Myers
*Attorney, Agent, or Firm*—Haseltine, Lake & Waters

[57] ABSTRACT

The invention provides novel esters of 1-(p-hydroxyphenyl)-2-(1'-methyl-2'-phenoxyethylamino)-1-propanol having better properties as vascular dilatators, than the corresponding 1-(p-hydroxyphenyl)-2-(1'-methyl-2-phenoxyethylamino)-1-propanol.

5 Claims, No Drawings

ESTERS OF 1-(P-HYDROXYPHENYL)-2-(1'-METHYL-2'-PHENOXYETHYLAMINO)-1-PROPANOL

The invention relates to a series of esters of v-(p-hydroxyphenyl)-2-(1'-methyl-2'-phenoxyethylamino)-1-propanol, of general formula I:

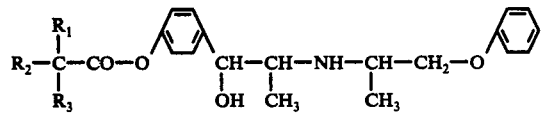
(I)

in which $R_1$, $R_2$, and $R_3$ are alkyl groups containing 1 to 4 carbon atoms. Compounds I show pharmacological characteristics surprisingly superior to those of the corresponding hydroxy derivatives II, 1-(p-hydroxyphenyl)-2-(1'-methyl-2'-phenoxyethylamino)-1-propanol (isoxysuprine):

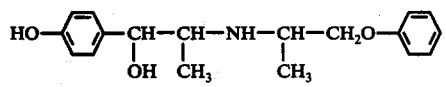
(II)

In fact, while the latter is among the better recognized vascular dilatators, it is characterized by, in addition to a proven therapeutic value, the drawback of activity of short duration and thus the necessity of multiple administrations. These cause short periods of intense dilatation followed by intervals of reduced hematic contribution; although a continuing and uniform vascular dilatation would ensure optimal oxygenation and thus a more effective treatment.

Now it has been found that with the new esters of formula I one attains a sufficiently intense and very long-lasting vascular dilatation. According to the invention, esters I may be prepared by the esterification of the phenolic function of 1-(p-hydroxyphenyl)-2-(1'-methyl-2'-phenoxyethylamino)-1-propanol (II) with reactive derivatives like chlorides, bromides, and anhydrides of aliphatic acids of general formula III:

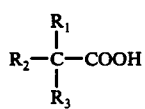
(III)

in which $R_1$, $R_2$, and $R_3$ are as reported above. The esterification may be performed in an apolar solvent at reflux (such as benzene, toluene, or an analogous aromatic hydrocarbon) in the presence of an organic base like triethylamine, or in pyridine at room temperature. The following tabel contains some data concerning the cardio-circulatory activity (evaluated by measuring the variation in pressure 1 to 2 days after the insertion of a catheter in the abdominal artery, according to the technique of J. R. Weeks and J. A. Jones (Proc.Soc.Exp.Biol., 104, 646, 1960)) and the acute toxicity of 1-(p-α,α-dimethylpropionyloxyphenyl)-2-(1'-methyl-2'-phenoxyethylamino)-1-propanol (LR 693) compared with 1-(p-hydroxyphenyl)-2-(1'-methyl-2'-phenoxyethylamino)-1-propanol (isoxysuprine).

| Compound | Acute Toxicity in rat DL 50 mg/Kg 05 | dose mg/Kg 05 | dose µM/Kg 05 | % maximal pressure decrease (mm Hg) | Hypotensive Activity Recovery to 50% (min) | to 75% (min) |
|---|---|---|---|---|---|---|
| LR693 | >5000 | 20 | 51.8 | 9.0±1.0 | 29.0±1.0 | *60.0±20.0 |
|  |  | 40 | 103.8 | 21.3±4.1 | 115.7±21.9 | 311.7±34.2 |
|  |  | 80 | 207.5 | 18.8±8.0 | 180.2±40.7 | 384.8±71.0 |
| Isoxysuprine | 1750 | 5 | 16.6 | 24.5±11.5 | 8.0±3.0 | 18.5± 6.5 |
|  |  | 10 | 33.2 | 25.3±3.6 | 79.8±32.6 | 105.0±42.9 |
|  |  | 20 | 66.4 | 28.7±4.9 | 46.4±13.8 | 110.4±29.4 |
|  |  | 40 | 132.8 | 21.8±2.1 | 34.0±12.8 | 197.5±59.5 |

*This number is not very reliable because of the difficulty in precisely evaluating a 75% recovery for a pressure lowered only 9mm Hg.

From compounds I, salts may be prepared in the usual manner with pharmaceutically acceptable acids, such as mineral acids like hydrochloric, hydrobromic, sulfuric, and nitric, or organic acids like acetic, propionic, oxalic, maleic, fumaric, and lactic.

According to the invention, compounds of general formula I, as their salts from the addition of acids, may be advantageously employed in human therapy to treat functional and organic vascular conditions of the peripheral circulation or as uterine relactants. They may be administered orally, rectally, or by injection by means of the appropriate pharmaceutical formulation as a solid, liquid, or suspension (tablets, capsules, vials, syrups, suppositories, and so on) in effective doses ranging from 0.030g to 0.090 daily.

The following examples illustrate the invention while not limiting it to only these cases.

EXAMPLE 1

1-(p-α,α-dimethylpropionyloxyphenyl)-2-(1'-methyl-2'-phenoxyethylamino)-1-propanol (LR 693)

To a stirred and cooled solution of 20g of 1-(p-hydroxyphenyl)-2-(1'-methyl-2'-phenoxyethylamino)-1-propanol in 60 ml of anhydrous pyridine are added dropwise 9.7g of pivaloyl chloride. The mixture is stirred for another two hours at room temperature after the addition is complete. Then it is poured over ice. The resulting white precipitate (23g) is isolated by filtration and crystallized from 340 ml of ethanol to yield 11.2g of a white, crystalline solid product, mp 153°–155° C.

EXAMPLE 2

1-(p-α,α-dimethylpropionyloxyphenyl)-2-1'-methyl-2'-phenoxyethylamino)-1-propanol (LR 693)

To a stirred and cooled solution of 15g of 1-(p-hydroxyphenyl)-2-(1'-methyl-2'-phenoxyethylamino)-1-propanol in 600 ml of anhydrous benzene containing 6.5g of triethylamine are added dropwise 7.8g of pivaloyl chloride. Following the addition, the mixture is held at reflux for 10 hours. The solid precipitate is then removed by filtration and the benzene solution evaporated to dryness after several washings with water. The residue is crystallized from 230 ml of ethanol to yield 13.5g of white, crystalline solid, mp 153°–155° C.

EXAMPLE 3

Tablets

| LR 693 : g. 0.03 | starch and talcum g.1.97 |

EXAMPLE 4

Vials

LR 693: g. 0.03 suspended in 2 ml bidistilled water.

We claim:

1. An ester of 1-(p-hydroxyphenyl)-2-(1'-methyl-2'-phenoxyethylamino)-1-propanol of formula I:

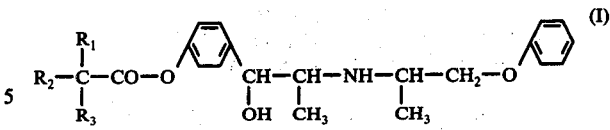

in which $R_1$, $R_2$, and $R_3$ are alkyl groups of from 1 to 4 carbon atoms, or a pharmaceutically acceptable salt thereof.

2. 1-(p-α,α-dimethylpropionyloxyphenyl)-2-(1'-methyl-2'-phenoxyethylamino)-1-propanol or a pharmaceutically acceptable salt thereof.

3. A vasodilating composition containing a vasodilating effective amount of 1-(p-α,α-dimethylpropionyloxyphenyl)-2-(1'-methyl-2'-phenoxyethylamino)-1-propanol together with a pharmaceutically acceptable expipient.

4. Method for effecting vasodilation in a patient which comprises administering to said patient a vasodilating amount of a pharmaceutical composition having as active ingredient 1-(p-α,α-dimethylpropionyloxyphenyl)-2-(1'-methyl-2'-phenoxyethylamino)-1-propanol in a pharmaceutically acceptable excipient.

5. A method according to claim 4 wherein the vasodilating amount of active ingredient is in the range of 0.030 to 0.090g daily.

* * * * *